(12) United States Patent
Markart

(10) Patent No.: US 6,441,898 B1
(45) Date of Patent: Aug. 27, 2002

(54) TEST STRIP AND MEASUREMENT DEVICE FOR ITS EVALUATION

(76) Inventor: Ernst Markart, Liebensteinstrasse 14, 81243 München (DE)

( * ) Notice: Subject to any disclaimer, the term of this patent is extended or adjusted under 35 U.S.C. 154(b) by 0 days.

(21) Appl. No.: 09/513,701

(22) Filed: Feb. 25, 2000

(51) Int. Cl.⁷ .................... G01N 21/01; A61B 5/00
(52) U.S. Cl. .................... 356/244; 356/440; 422/82.05; 422/58; 435/808
(58) Field of Search .................... 356/244, 246, 356/440, 319, 326; 250/339.07, 343; 422/102, 99, 100, 104, 61, 82.05, 58; 436/164, 172, 165; 435/14

(56) References Cited

U.S. PATENT DOCUMENTS

| | | | | |
|---|---|---|---|---|
| 2,694,852 A | * | 11/1954 | Rogers | |
| 3,049,796 A | * | 8/1962 | Pall | |
| 4,387,972 A | * | 6/1983 | Valencia | 356/244 |
| 4,441,793 A | * | 4/1984 | Elkins | 356/244 |
| 5,290,705 A | * | 3/1994 | Davis | 436/164 |
| 5,453,252 A | * | 9/1995 | Truett | 422/104 |
| 5,519,218 A | * | 5/1996 | Chang | 250/339.07 |
| 5,764,355 A | * | 6/1998 | Gagnon et al. | 356/244 |
| 5,786,226 A | * | 7/1998 | Bocker et al. | 436/164 |
| 6,121,052 A | * | 9/2000 | Hoult | 436/165 |
| 6,280,690 B1 | * | 8/2001 | Tadion | 422/102 |

* cited by examiner

*Primary Examiner*—Hoa Q. Pham
(74) *Attorney, Agent, or Firm*—McCormick, Paulding & Huber LLP

(57) ABSTRACT

In a test strip for the optical determination of the concentration of a substance in a liquid, especially for blood sugar determination, including a strip-shaped carrier with a reaction field, defined by opaque material on the carrier, containing a reagent carrying medium, which reagent carrying medium upon wetting with the fluid to be investigated changes in regard to its reflectivity or transmissivity, the carrier consists of an optically transparent material onto which a thin-layered carrying medium containing the reagent is applied.

32 Claims, 2 Drawing Sheets

TEST STRIP AND MEASUREMENT DEVICE FOR ITS EVALUATION

FIELD OF THE INVENTION

The invention concerns a test strip for the optical or electrical current determination of the concentration of a substance in a liquid, especially for blood sugar determination, including a strip-shaped carrier with a reaction field which contains a reagent, and which upon wetting with the substance to be investigated changes the optical transmissivity or reflectivity or electrical conductivity of the reaction field.

BACKGROUND OF THE INVENTION

For blood sugar determination, such as a diabetic under certain circumstances must take several times a day, the patient has to stick himself in the finger to obtain blood, a drop of which is applied to the test strip. This procedure is not only unpleasant for the patient, but in the course of time leads to the finger becoming so scarred that the obtaining of a sufficiently large drop of blood becomes difficult. Therefore, it becomes desirable to have test strips making possible a sufficiently precise measurement from a very small amount of blood. In connection with this, it is to be taken into account that the test strips, because of being hand manipulated in a measuring procedure, cannot be made as small as might otherwise be desired. Also, to be taken into account is that the test strips should be constructed in such a way that they can be made by means of a continuous process.

The invention, therefore, has as its object the provision of a test strip of the above-mentioned kind which on one hand delivers a trouble free measuring result with a small volume of the investigated liquid and which on the other hand can be made in a rational way.

SUMMARY OF THE INVENTION

For the solving of the above object, it is proposed in accordance with the invention that the test strip carrier be made of an optically transparent material onto which a reagent containing thin layered reaction carrier is applied. This reaction carrier is preferably a paint, but can also be a paste or a thin paper.

In customary test strips, the reagent is contained in a so-called membrane, consisting of a felt, foam material, or textile piece, which absorbs the fluid to be investigated. Therefore, a substantial amount of liquid is needed to soak the entire membrane. In contrast to this, in the inventive solution, the thin layered reaction carrier itself takes on only very little liquid. The fluid dropped onto the reaction field reacts directly with the reagent. Thereby, in comparison to the usual test strip only a very small amount of liquid is needed for the desired concentration determination. Further, the making of the strips is of utmost simplicity, since only one web is needed with the carrier material, onto which web the reagent containing reaction carrier is applied as paint or paste, and from which web the test strips subsequently can be cut.

Whereas, in customary test strips, the size of the measuring field is determined by the dimensions of the membrane piece, in the case of the inventive solution the reaction field is not sharply limited. To obtain a clearly limited reaction field and measuring field for the optical measurement, it is advantageous if the reaction field is bordered by a diaphragm, for example, of two opaque diaphragm strips running along the longitudinal edges of the strip or of an opaque surrounding diaphragm. This diaphragm or the diaphragm strips can simply be printed onto the carrier web, for example, with black color. Advantageously, the diaphragm strips are first printed onto the carrier web, and then after that the reagent containing reaction carrier is applied. The above described advantage of the transparent carrier web provided with a diaphragm is obtained also if the reaction carrier is formed by a customary membrane.

The transparent carrier web offers the possibility of providing on the carrier web itself a reference surface which advantageously is arranged in the surface area of at least one of the diaphragm strips. Therefore, with the help of a corresponding optic system, upon the depositing or insertion of the test strip into the measuring device, a calibrating measurement can be carried out at the reference surface. This has not only the advantage that the reference measurement and the actual concentration measurement can be performed at practically the same time, but also that the spacing of the reference surface from the measuring optic system is identical to the spacing of the reaction field from the measuring optic system. If, for example, the test strip does not lie entirely flatly on the strip support surface, this error occurs in the same way for the reference surface as well as for the reaction field, so that the error is compensated for by the comparing measurements.

Preferably, the reference surface is applied directly onto the carrier web material and indeed before the printing of the diaphragm strips.

Advantageously, the diaphragm strips and/or the reference surface are provided on the same side of the carrier web as is the reagent containing paint. The diaphragm can, however, also be printed onto the opposite carrier web side.

To achieve a uniform distribution of even the smallest liquid drop over the reaction field, the reaction field can be covered by a hydrophilic material. For this can be used, for example, a finely woven textile or a fine netting having practically no thickness so as to "suck up" very little liquid in comparison to the customary membranes. To, on one hand, limit the liquid absorption by the hydrophilic material and, on the other hand, to not make difficult the continuous manufacture of the test strips, the hydrophilic material can be made or be treated so as to have hydrophobic surface portions in which surface portions no liquid can be absorbed. At the same time, there results a spatial limiting of the blood application location over the measuring optic system.

To limit the blood application area and to protect the reaction field, the surface area of the test strip containing the reaction field can be provided with a hydrophobic cover having a drop application opening. In this case, the drop application opening does not have to lie directly over the measuring field onto which the measuring optic system is directed. In a preferred embodiment of the invention, the drop application opening is on the contrary provided adjacent to a longitudinal end of the test strip. This provides the possibility of inserting the test strip into the measuring device and not until then applying the fluid to be investigated, for example, by stripping off a blood drop in the region of the drop application opening at the end of the strip. Because of the hydrophilic material, the fluid to be investigated is then transported from the drop application opening to the area of the reaction field detected by the measuring optic system. The cover is preferably a plastic foil.

The invention further concerns a measuring device for the optical determination of the concentration of a substance in a liquid, especially for blood sugar determination, by means of a test strip of the previously described kind, wherein the measuring device has a housing with a strip support surface, a measuring optic system or contacts arranged below the strip support surface, an indicator mechanism, an operating field and an evaluation and control circuit. According to the invention, the measuring optic system includes three optical sensors for the optical measurement, of which sensors two are directed onto the reaction field and one is directed onto the reference surface. This makes possible the simultaneous measurement of the reference surface and of the reaction field, so that not only is the carrying out of the measurement simplified, but also the exclusion of error sources is possible.

In a preferred embodiment, the sensors directed toward the reaction field are arranged behind one another in a longitudinal direction of a test strip lying on the strip support surface. If, for example, the liquid is applied in the above-described way to the drop application opening provided at the longitudinal end of the strip and is transported by the hydrophilic material in the direction toward the reaction field, a measuring signal from the two spaced sensors further give the assurance that the region of the reaction field lying between the second sensor and the drop application opening is entirely wetted with the fluid to be investigated and that the output signal of the first sensor lying between the second sensor and the drop application opening corresponds to a fully wetted surface.

In a similar way in case of a test strip to be measured by way of electrical current, a test can be made as to whether the test field has been sufficiently wetted with the liquid to be investigated, if the electrodes for an electrical current measurement of the measuring field of the test strip lie between the drop application location and an optical measuring point. If at the optical measuring point, it is determined by the help of an associated optical sensor that the liquid to be investigated has reached the optical measuring point, it can be taken from that that a sufficient amount of the liquid to be investigated has also reached the measuring field in which the measuring electrodes lie.

To be able to compensate for a change in the sensitivity of the optical sensors with or in dependence on temperature, in accordance with the invention it is proposed that a reference surface is provided above the strip support surface for balancing of the optical sensors. In this case, the evaluation and control circuit can be so made that it carries out the comparison at pre-given time intervals or that the comparison process is carried out in dependence on a pre-given temperature change, which change is determined by the help of a temperature sensor provided in the measuring device.

The reference surface can be formed directly onto a cover fixed to the housing and extending over the strip support surface. Another possibility is that the reference surface can be formed on a key which is so arranged on the housing above the strip support surface so that it is movable between a position at which it presses the test strip against the support surface and a test strip freeing position. This key can be at least in part transparent.

Preferably the evaluation and control circuit is so formed that by means of the optical sensors different reflectivities/transmissivities of the field are recognizable. This offers the possibility of calibrating the measuring optic system of the measuring device so that an actual measured reflectivity/transmissivity of the measuring field also corresponds actually to a given concentration of the investigated substance. The functional correlation between the reflectivity/transmissivity detected by the measuring optic system and the concentration values of the investigated substance is stored in the evaluation and control circuit.

The calibration can be done in that a card can be arranged on the strip support surface and have calibration fields associated with the individual optical sensors, the calibration fields having reflectivity/transmissivity values each corresponding to a given concentration of the investigated substance, so that the actual measured reflectivity/transmissivity values of the calibration field can be compared with the corresponding values according to the stored functional relationship and so that upon the appearance of a difference a corresponding correction factor can be determined by means of which a test strip measured reflectivity/transmissivity value can be corrected.

The calibration card can moreover carry a code evaluatable by the evaluation and control circuit, which code, for example, contains information about the selected measuring program or the batch from which the test strip to be measured came. This code can be formed with the help of the calibration fields. The calibration card can also carry other information. Especially, further color fields can be provided which make possible a visual comparison between the measuring field of a test strip and one of the color fields, so at least a coarse determination of the concentration can be carried out visually.

BRIEF DESCRIPTION OF THE DRAWINGS

Further features and advantages of the invention will be apparent from the following description, which in combination with the accompanying drawings explains the invention by way of exemplary embodiments. The drawings are.

DETAILED DESCRIPTION OF PREFERRED EMBODIMENTS

Figure 1:
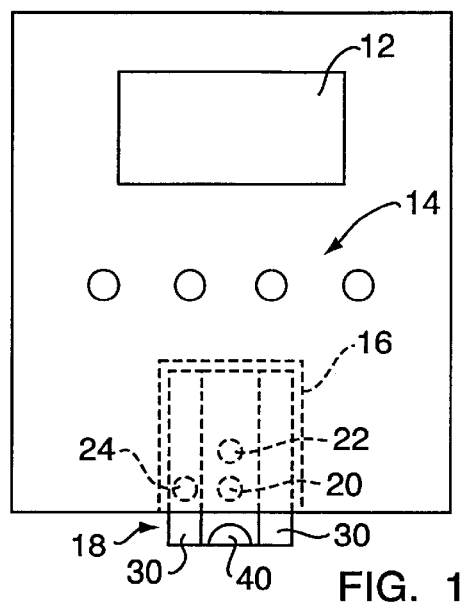
FIG. 1—a schematic plan view of a measuring device according to the invention.

The measuring device shown schematically in FIG. 1 has a housing 10 with an indicator field 12, which in customary way can be made from an LCD-screen, and with an operating field 14. Under the cover surface of the housing 10 is a strip support surface 16, shown in broken line, onto which a test strip 18 can be laid. The test strip is either inserted into a slot provided on the front side of the housing 10 or a cover is formed over the upper portion of the housing which can be lifted up or pushed away in order to give free access to the strip support surface 16.

Below the strip support surface 16 and inside of the housing is a measuring optic system including at least two, and in the illustrated example, three optic sensors 20, 22 and 24 which will be dealt with in more detail later.

The construction of the test strips illustrated in FIGS. 2 and 3 can be best explained with reference to FIG. 4. Each test strip 18 has a carrier web 26 made of an optically transparent material. On the carrier web material are two diaphragm strips parallel to the edges 28 of the carrier web 26, which diaphragm strips, for example, are made of a black material and are printed onto the carrier web 26. In the intervening space between the diaphragm strips 30 the carrier web 26 is covered by a layer 34 of paint, which, for example, contains the chemicals necessary for the concentration determination and which in the illustrated embodiment also extends over the diaphragm strips 30 although this is not necessary. The region between the two diaphragm strips represents the actual reaction field.

Figure 2:
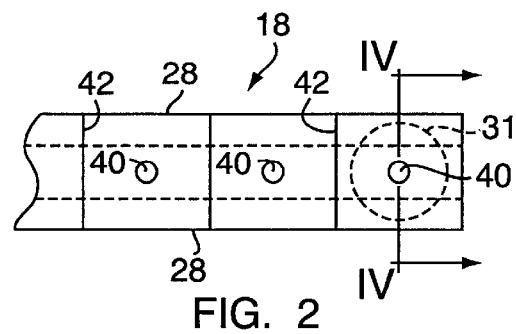
FIG. 2—a plan view of a plurality of yet together hanging test strips according to a first embodiment of the invention.
Figure 3:
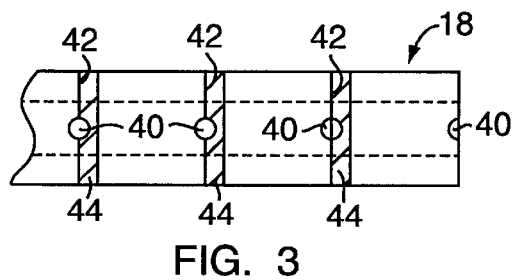
FIG. 3—a view corresponding to FIG. 2 of a test strip row according to a second embodiment of the invention.

Applied to the carrier web material are two diaphragm strips 30 extending along the longitudinal edges 28 of the strip, or a single diaphragm 31 as shown by the broken lines in FIG. 2, which, for example, are made of black color and are printed onto the carrier web material. Between the left diaphragm strip 30 in FIG. 2 and the carrier web 26 is a reference surface 32 which, for example, is made of a white color and is used as a white standard in the measuring device 10. In the intermediate space between the diaphragm strips 30, the carrier 26 is covered by a paint layer 34 which, for example, contains the chemical compound required for the concentration determination and which in the illustrated embodiment also extends over the diaphragm strips 30, although this is not necessary. This area between the two diaphragm strips represents the actual reaction field.

Over this reaction field lies a layer 36 made of a hydrophilic material, for example a finely woven net or textile. This net 36 serves to distribute the dropped on liquid uniformly over the reaction field.

The entire arrangement as so far described is covered by a hydrophobic layer 38, such as for example a plastic foil material, having a drop application opening 40 lying in the region between the diaphragm strips 30.

In the making of the test strips 18, the diaphragm strips 30 are first printed onto a continuous carrier web 26 as continuous webs of color material. Thereafter, the reagent containing paint 34 or other reaction carrier is applied, whereupon the layers 36 and 38 of hydrophilic and hydrophobic material are applied. Finally, from this arrangement the individual test strips 18 are separated. In the illustrated embodiment of FIG. 2, the separation lines run perpendicular to the diaphragm strips and are located midway between adjacent ones of the drop application openings which are formed in the cover foil 38 before the application of the cover foil 38. In the embodiment according to FIG. 3, the separation lines 42 run through the drop application openings 40, so that only a semi-circular drop application opening comes to lie at one end of each test strip. In the embodiment according to FIG. 3, an area 44, illustrated as a cross-hatched area, is cut out as waste so that each strip has a drop application opening only at one end.

The use of the test strip 18 made in accordance with FIG. 3 will now be explained in more detail.

The test strip 18 is inserted into the measuring device, as shown in FIG. 1 so that the end of the strip having the drop application opening 40 extends out of the measuring device 10. The user can now apply a drop of the fluid to be investigated, for example, a drop of blood, onto the semi-circular shaped drop application opening 40 on the exposed material of the test strip 18. The user can also first apply the blood to the test strip and then insert the strip into the device. The hydrophilic layer causes the applied liquid to spread over the reaction field lying between the two diaphragm strips 30 and this distributed liquid reacts with the reagents contained in the paint layer 34, which leads to a change in the reflectivity of the reaction field, which change can be captured by the sensors 20 and 22 located under the strip support surface 16. When it is determined by way of an output signal from the sensor 22 that the liquid has reached the region of the sensor 22, one can assume that the entire region sensed by the sensor 20 has been uniformly wetted with the liquid. The illustrated arrangement thereby offers the possibility of controlling the wetting of the reaction field. The two sensors 20 and 22 can, however, be arranged next to one another, which in itself is already known, to likewise confirm a uniform wetting of the observed reaction field.

The reference surface 32 comes to lie over the sensor 24 as a white standard, so that with the help of the sensor 24, a calibrating measurement can be carried out. The advantage of this arrangement resides in that the reference measurement and the calibrating measurement can be carried out without the test strip 18 being moved between the two measurements. Further, since the reference surface 32 and the reaction field 34 necessarily have the same spacing from the sensor 24 on one hand and from the sensors 20 and 22 on the other hand, no spacing error can appear, as can appear in the case of customary devices with a white standard fixedly integrated into the measuring device, if, for example, the test strip does not lie flatly on the strip support surface.

Figure 4:
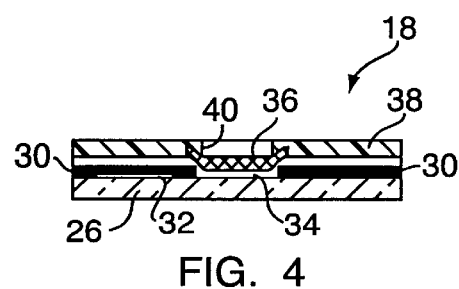
FIG. 4—a sectional view through a test strip taken along the line IV—IV in FIG. 2.
Figure 5:
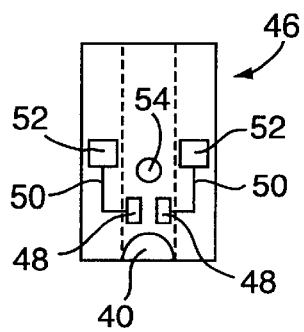
FIG. 5—a schematic plan view of a test strip for measurement by way of electrical current.

The test strip 46 illustrated in FIG. 5 is essentially made exactly the same as the one illustrated in FIG. 4. However, lying within the measuring field, that is, embedded in the paint layer 34, are two measuring electrodes 48, each of which is connected by a conductor 50 with a contact surface 52. These contact surfaces 52, upon insertion of the test strip into the strip receiver of the measuring device 10 come into contact with nonillustrated complementary contact elements of the measuring device, so that a current can be measured, which current flows between the measuring electrodes 48 upon wetting of the measuring field with the fluid to be investigated.

As shown in FIG. 5, the measuring electrodes 48 are arranged between the drop application opening 40 and an optical measuring point 54. If the liquid to be investigated is dropped at 40 onto the test strip 56, it is transported by the hydrophilic layer 36 to the measuring field in which the measuring electrodes 48 lie. If, for example, with the help of the optical sensor 22 of the measuring device 10, a change in the reflectivity/transmissivity is detected at the optical measuring point 54, this is proof that the measuring field containing the electrodes 48 has been supplied with sufficient liquid and that a stable measuring operation can be made.

Figure 6:
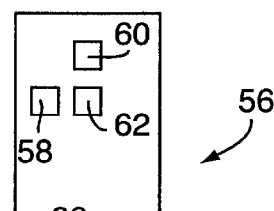
FIG. 6—a schematic plan view of a calibration card for calibrating the measuring optic system.
Figure 7:
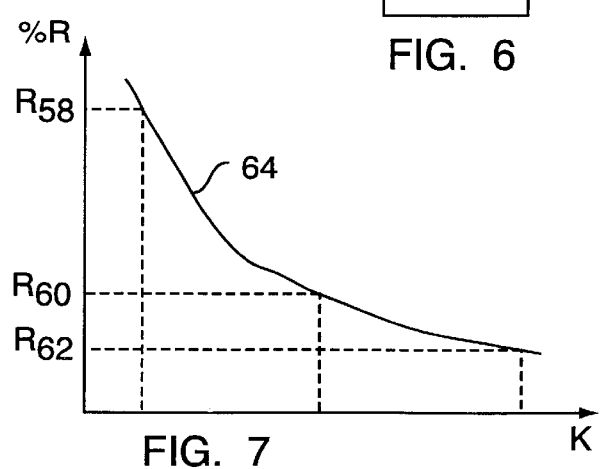
FIG. 7—a schematic illustration of the relationship between the reflectivity and the concentration of the substance to be investigated.

FIG. 6 shows a calibration card indicated generally at 56. It contains three calibration fields 58, 60, 62 associated with the three sensors 24, 22, 20 of the measuring device. Each of the calibration fields 58, 60, 62 has a reflectivity corresponding to a given concentration of the looked for substance in the fluid to be investigated. The correspondence between the reflectivity and the concentration of the looked for substance is reproduced, for example, by the illustrated curve 64 of FIG. 7, wherein the abscissa represents the concentration and the ordinate reflectivity. This curve 64 is stored in the evaluating and control circuit of the measuring device. The reflectivity values of the calibration fields 58, 60, 62 are indicated in FIG. 7 at R58, R60, and R62. If the calibration card 56 is inserted into the measuring device 10 so that the sensors 24, 22, 22 are directed onto the calibration fields 58, 60, 62, distinct reflectivity values are measured, which are not necessarily identical to the values R58, R60, and R62, in which case an error would be produced in the concentration determination. If there exists such a difference, a correction factor is produced for use in compensating for the measuring error arising from the characteristics of the optical sensors, when subsequently a test strip is measured.

On the rear side of the calibration card 56 is provided, according to FIG. 6, a homogenous reference field 63 which forms a unitary standard for all three sensors 20, 22 and 24.

The calibration card 56 can, for example, be provided with a test strip package and they are usually newly created for each batch of test strips, since the test strips from batch to batch can differ.

The calibration fields can also be detailed to form a code, which code is transmitted to the measuring device by the calibration card 56 and, for example, makes a statement about the type of program to be chosen or about the batch. This code, however and self evidently, can also be printed onto the calibration card 56 in other ways.

Further, color fields 66, 68, 70 are arranged on the calibration card 56, which color fields, for example, make possible a visual comparison with a test field, so at least a coarse visual determination of the concentration of the looked for substance can be made.

Figure 8:
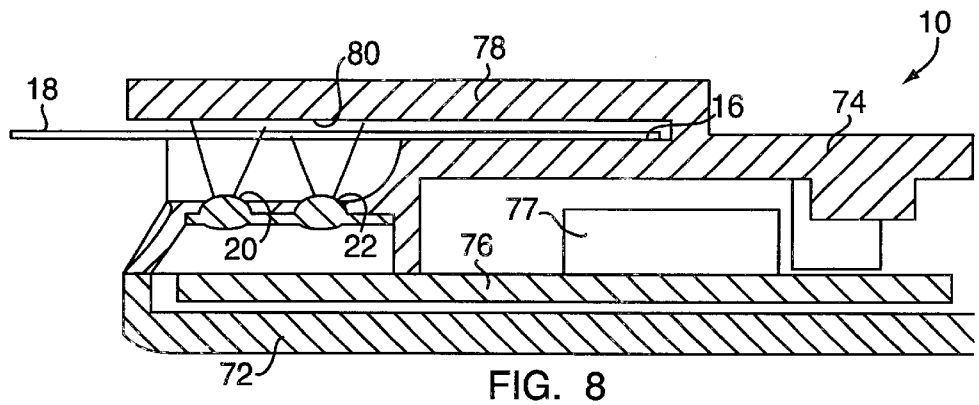
FIGS. 8–10—are each a schematic partial section through respective different exemplary embodiments of the measuring device in the area of the strip support surface.

FIG. 8 shows a schematic section through a portion of the measuring device in the area of the strip support surface 16. The housing 10 of the measuring device includes a lower portion 72 and an upper portion 74. Inside of the housing 10 is a plate 76 which carries the schematically illustrated evaluation and control circuit 77. Below the strip support surface 16 are two optical sensors 20 and 22 in the upper portion 74. Over the strip support surface 16, on which the test strip 18 lies, a cover 78 fixed to the housing extends parallel in a spaced relationship to the strip support surface 16. The cover 78 on its underside facing the strip support surface 16 has a reference surface 80 which serves to correct changes in the output signals of the optical sensors due to aging or temperature dependency or also due to soiling, in that all of the optical sensors can be balanced through the reference surface 80 to a given standard either physically or by computation.

Figure 9:
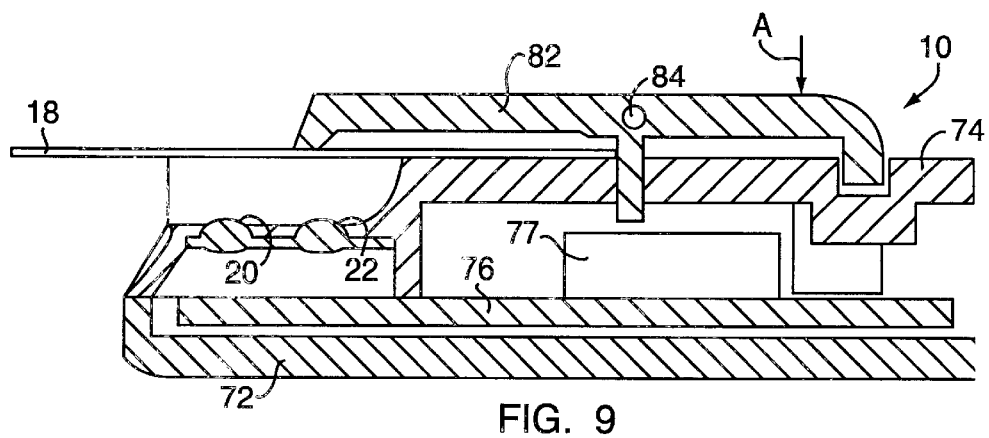

In the embodiment illustrated in FIG. 9, parts which are similar to those previously described are again indicated with the same reference numbers. The embodiment differs from that of FIG. 8 in that the cover for the strip support surface 16 is not fixed relative to the housing, but is provided by a key 82 which is supported by the upper housing portion 74 for pivotal movement about an axis 84. In the position illustrated in FIG. 9, the key holds the test strip 18 against the strip support surface 16, so that the test strip 18 is held in place during a measurement. If the key, by pressure applied to its rearward section, is pivoted clockwise in the direction of the arrow A, the test strip 18 is freed and can, for example, fall by itself from the measuring device. The reference surface 18 can, like in the case of the cover 78 fixed to the housing, be arranged on the underside of the key 82. The key 82 can also be made either entirely or partially of a transparent material.

Figure 10:
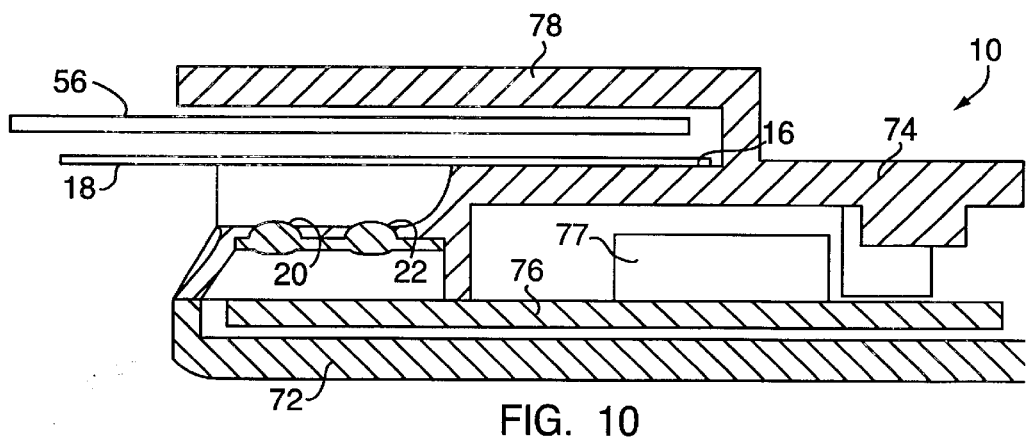

In conclusion, FIG. 10 shows a variation of the embodiment illustrated in FIG. 8, and wherein the cover 78 fixed to the housing merely has a somewhat larger spacing from the strip support surface 16 so that the calibration card and a test strip 18 can be inserted into the measuring device at the same time. The calibration card 56, for example, stays in the measuring device for so long as strips from a given strip package or strip batch are use. When strips of a new batch are used, a new calibration card is inserted.

What is claimed is:

1. A test strip for optically determining the concentration of a substance in a liquid, said test strip comprising a strip-shaped transparent carrier with upper and lower faces; opaque material on and covering a portion of one of said faces of the carrier, said opaque material defining a reaction field on said carrier free of said opaque material and with said opaque material being located on at least two sides of said reaction field, a layer of reagent carrying medium carried by said carrier which layer of reagent carrying medium is located above said upper face of the carrier and covers said reaction field, which layer of reagent carrying medium upon wetting with the liquid to be investigated changes in regard to its optical reflectivity or transmissivity.

2. A test strip according to claim 1, wherein the reagent carrying medium is a paint.

3. A test strip according to claim 1, wherein the reagent carrying medium is a paste.

4. A test strip according to claim 1, wherein the reagent carrying medium is a piece of thin strip material.

5. A test strip according to claim 1, wherein the opaque material located on at least two sides of the reaction field is provided by two diaphragm strips of opaque material running along the longitudinal edges of the carrier.

6. A test strip according to claim 5, wherein the opaque material is provided on the side of the carrier which is opposite from the side carrying the reagent carrying medium.

7. A test strip according to claim 1, wherein the opaque material surrounds the reaction field.

8. A test strip according to claim 1, wherein the opaque material is printed onto the carrier.

9. A test strip according to claim 1, wherein the layer of reagent carrying medium covers at least a portion of the opaque material.

10. A test strip according to claim 1, wherein a layer of reference material is carried by the carrier and covers a small area of the carrier to provide an optical reference surface which can be sensed by an optical sensor located below the carrier.

11. A test strip according to claim 10, wherein the reference material is printed onto the upper face of the carrier so that the reference surface can be sensed through the transparent carrier by a sensor located below the carrier.

12. A test strip according to claim 10, wherein the opaque material and the reference surface are provided on the same side of the carrier as the reagent carrying medium.

13. A measuring device for optically determining the concentration of a substance in a liquid, by means of a test strip according to claim 10, said measuring device including a housing with a strip support surface, a measuring optic system arranged below the strip support surface, an indicator apparatus, an operating field and an evaluation and control circuit, said measuring optic system having at least three optical sensors of which two are directed onto the reaction field and one of which is directed onto the reference surface.

14. A measuring device according to claim 13, wherein the sensors directed onto the reaction field are arranged behind one another in the longitudinal direction of a test strip lying on the strip support surface.

15. A measuring device according to claim 13, wherein a reference surface is provided above the strip support surface for balancing the optical sensors.

16. A measuring device according to claim 15, wherein the evaluation and control circuit is so formed that it automatically carries out the balancing process at pre-given time intervals.

17. A measuring device according to claim 15, wherein the measuring device has a temperature sensor and the evaluation and control circuit is so formed that the balancing process is carried out in dependence on a pre-given temperature change.

18. A measuring device according to claim 15, wherein the reference surface is provided on a cover fixed relative to the housing and extending over the strip support surface.

19. A measuring device according to claim 13, wherein a key is arranged on the housing above the strip support surface, which key is movable between a first position in which it clamps the test strip against the strip support surface and a position at which the test strip is freed.

20. A measuring device according to claim 19, wherein at least a part of the key is transparent.

21. A measuring device according to claim 19, wherein the reference surface is formed on the key.

22. A measuring device according to claim 13, said device further comprising three optical sensors for respectively sensing a part of said reaction field, said reference surface, and one other area of said test strip different from said part of the reference field and the reference surface, and wherein the evaluation and control circuit is so formed that the reflectivity/transmissivity of each of said part of the reaction field, the reference surface, and the other area of the test strip is recognizable by the evaluation and control circuit.

23. method for the calibration of the measuring optic system of a measuring device according to claim 20, wherein the evaluation and control circuit stores a functional relationship between the reflectivity/transmissivity sensed by the measuring optic system and the concentration value of the substance to be investigated, and wherein a card is arranged over the strip support surface with calibration fields associated with the individual optical sensors, with each of the calibration fields having a reflectivity/transmissivity corresponding to a given concentration of the substance to be investigated, the actually measured reflectivity/transmissivity values of the calibration fields being compared with the corresponding values according to the stored functional relationship and upon the appearance of a difference determining a corresponding correction factor by means of which the measured reflectivity/transmissivity value of the test strip is corrected.

24. A method according to claim 23, wherein the card carries a code evaluatable by the evaluation and control circuit.

25. A method according to claim 24, wherein the code is formed by the calibration fields.

26. A method according to claim 23, wherein the card has further color fields each of which corresponds to a given concentration of the substance to be investigated, and which can be visually compared with the reaction field of a test strip wetted by the liquid to be investigated.

27. A test strip according to claim 1, wherein the reaction field is covered by a hydrophilic material for uniformly distributing over the reaction field the liquid to be investigated.

28. A test strip according to claim 27, wherein the hydrophilic material is a finely woven textile.

29. A test strip according to claim 27, wherein the hydrophilic material is surrounded by a hydrophobic material which absorbs essentially none of the liquid.

30. A test strip according to claim 1, wherein the surface area of the test strip containing the reaction field is provided with a hydrophobic covering having a drop application opening.

31. A test strip according to claim 30, wherein the drop application opening is arranged adjacent to a longitudinal end of the test strip.

32. A test strip according to claim 30, wherein the hydrophobic covering is a plastic foil.

* * * * *

UNITED STATES PATENT AND TRADEMARK OFFICE
CERTIFICATE OF CORRECTION

PATENT NO.    : 6,441,898 B1
DATED         : August 27, 2002
INVENTOR(S)   : Ernst Markart It is certified that error appears in the above-identified patent and that said Letters Patent is hereby corrected as shown below:

Column 9,
Line 31, -- A -- should be inserted before "method"
Line 32, "claim 20" should read -- claim 13 --

Signed and Sealed this

Twenty-first Day of January, 2003

JAMES E. ROGAN
*Director of the United States Patent and Trademark Office*